United States Patent
Römisch et al.

[11] Patent Number: 5,869,231
[45] Date of Patent: Feb. 9, 1999

[54] METHOD FOR REPRODUCIBLY DETERMINING THE COMPONENTS OF LACRIMAL FLUID

[75] Inventors: Jürgen Römisch; Eckhard Schüler, both of Marburg; Klaus Habenstein, Wetter; Jürgen Lindner, Marburg, all of Germany

[73] Assignee: Behring Diagnostics GmbH, Marburg, Germany

[21] Appl. No.: 949,779

[22] Filed: Oct. 14, 1997

Related U.S. Application Data

[63] Continuation of Ser. No. 693,500, Aug. 7, 1996, abandoned, and Ser. No. 325,495, Oct. 19, 1994, abandoned.

[30] Foreign Application Priority Data

Oct. 21, 1993 [DE] Germany .................. 43 35 961.2

[51] Int. Cl.$^6$ .............. C12Q 3/00; A61M 35/00
[52] U.S. Cl. .................. 435/4; 128/760; 604/1; 604/2; 604/19; 604/245; 604/246; 604/289; 604/290; 604/294; 604/300; 604/301; 604/302; 292/DIG. 5; 4/619; 514/912; 514/913; 514/915

[58] Field of Search ................. 514/912, 913, 514/915; 4/619, 621; 292/DIG. 5; 604/1, 2, 19, 245, 246, 289, 290, 294, 300, 301, 302; 435/4; 128/760

[56] References Cited

U.S. PATENT DOCUMENTS

| 4,269,197 | 5/1981 | Gilbard . |
| 4,526,178 | 7/1985 | Opel ................................ 128/760 |
| 4,564,518 | 1/1986 | Rosenbaum . |
| 5,171,307 | 12/1992 | Sanning ................. 604/294 |

FOREIGN PATENT DOCUMENTS

WO 91/06242  5/1991  WIPO .

*Primary Examiner*—Helen Pratt
*Attorney, Agent, or Firm*—Finnegan, Henderson, Farabow, Garrett & Dunner, L.L.P.

[57] ABSTRACT

The invention relates to a sampling kit for obtaining, in a rapid and gentle manner, a defined volume of lacrimal fluid for the purpose of reproducibly determining components of the lacrimal fluid.

15 Claims, 2 Drawing Sheets

METHOD FOR REPRODUCIBLY DETERMINING THE COMPONENTS OF LACRIMAL FLUID

This application is a continuation of application Ser. No. 08/693,500 filed Aug. 7, 1996, now abandoned and a continuation of application Ser. No. 08/325,495 filed Oct. 19, 1994, now abandoned.

The invention relates to a sampling kit for obtaining, in a rapid and gentle manner, a defined volume of lacrimal fluid for the purpose of reproducibly determining components of the lacrimal fluid.

Concentrations of different components can change during the course of the pathogenesis of ophthalmological disorders. These components include enzymes, such as proteases, decreases or increases in the activities of which can provide pointers to irritation or damage, especially in the anterior region of the eye. The quantification of particular parameters in lacrimal fluids in this way can be used both for diagnosing a disorder and for monitoring the course of a therapy.

Methods exist for obtaining lacrimal fluid, such as sampling using capillaries, which can be employed in species having a high level of lacrimal secretion. This procedure requires practice, since there is the danger of damaging the eye with the capillary, particularly if the sampling lasts for several minutes or more. This is especially the case when small volumes are available, as in the course of some disorders (dry eye syndrome), or in species, such as the rabbit, which naturally have a very low level of lacrimal secretion.

The method of obtaining lacrimal fluid using "Schirmer" strips, based on soaking up into a filter or absorbent paper, is likewise not optimal. In this method, the filter strip comes into direct contact with the surface of the cornea or conjunctiva for several minutes so that there is the danger of damaging these tissues. In addition to this, cells can be detached and, when adhering to the filter strip, can give rise to erroneous measurement results.

In addition to this, the quantification of parameters is rendered more difficult by the fact that it is scarcely possible to take a sample of defined volume since the filter strip has a large surface area. While it is possible to determine the volume which has been absorbed, this requires differential weighing. These steps lead to the loss of time and provide additional opportunities for errors in the subsequent determination of a parameter under test.

The underlying object of the present invention is therefore to improve the isolation of lacrimal fluid such that it can, on the one hand, be carried out rapidly and in a manner which is gentle for the test subject, and, on the other hand, permits a high degree of reproducibility in the qualitative and quantitative determination of components in the lacrimal fluid which has been isolated by making it possible to use a defined volume of lacrimal fluid in the test. It was a particular intention to improve the isolation of lacrimal fluid in those animal species, e.g. the rabbit, which naturally have a very low level of lacrimal secretion.

The object is achieved by providing a suitable sampling kit and a special method of sampling.

The invention thus relates to a sampling kit for obtaining a defined volume of lacrimal fluid, which kit contains a fluid which is well-tolerated by the eye and is suitably bottled, and a shaped absorbent material for the sampling.

Preferably, the shaped absorbent material comprises a non-absorbent carrier material and an absorbent layer, which serves for the sampling, fixed on the carrier material.

In a particularly preferred embodiment, the sampling kit contains a flexible plastic strip having an absorbent layer, which is limited in its surface area and height, fixed on the plastic strip.

The invention furthermore relates to a process for obtaining lacrimal fluid, wherein a defined volume of a fluid which is well-tolerated by the eye is applied to the surface of the eye or into the conjunctival sac, and subsequently a defined volume of the lacrimal fluid amplified in this way is removed.

The volume introduced into the eye, and the filter paper, can be matched to the necessary tear volume which is required for use in the subsequent test mixture in order to be able to detect the component. Volumes of between 1 and 500 $\mu l$ (depending on the size of the human eye or of that of other species) should be introduced, with, in the case of humans, primates, rabbits, cats or dogs, between 2 and 200 $\mu l$ being preferred, between 3 and 100 $\mu l$ being particularly preferred and between 5 and 30 $\mu l$ being very particularly preferred.

Defined volumes can be obtained by absorbing with an absorbent material which is matched, in its dimensions, to the dripped-on volume and which permits rapid sample removal. In this context, the size dimensions of the absorbent material always have to be such that the maximum absorbable volume is exceeded by the quantity of amplified lacrimal fluid, since only in this way is it possible to ensure that a reproducible volume of lacrimal fluid is removed.

Advantageously, the sizing of the absorbent material is also matched to the tear volume which is naturally to be expected in a particular species.

Figure 1A:
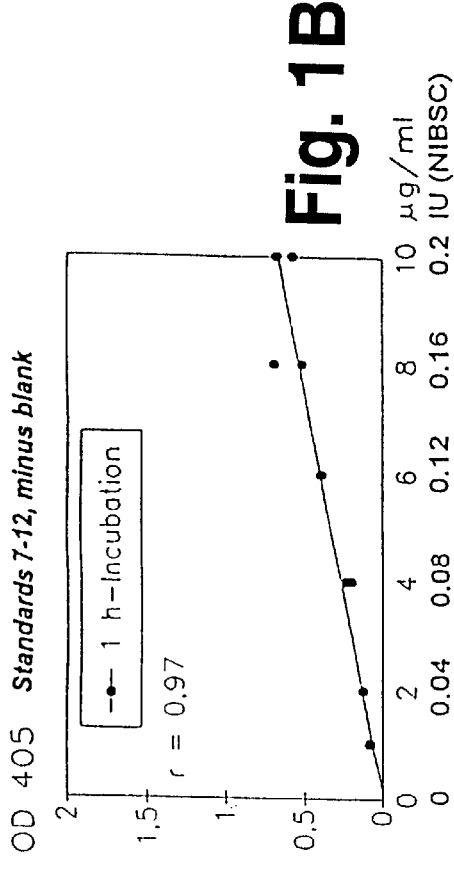
FIG. 1 shows standard curves of human plasmin activity and concentration (sub-standard BW Lot 920801).
Figure 1B:
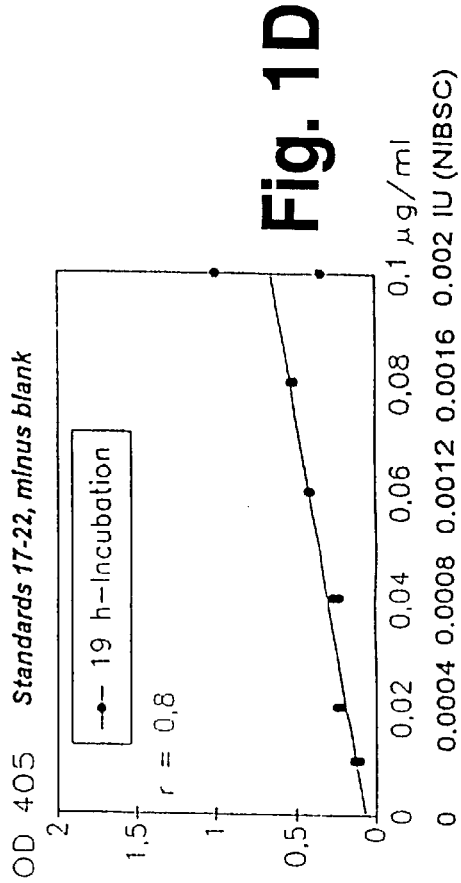
Figure 1C:
Figure 1D:
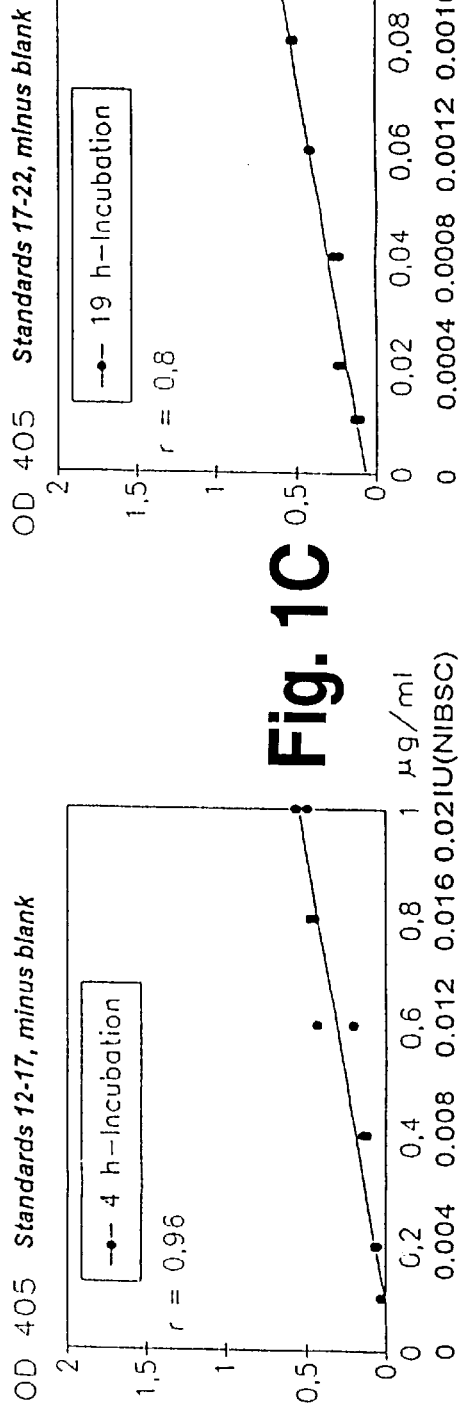

In practice, the preferred approach using the above-described materials is as follows:

A defined volume of a fluid which is well-tolerated by the eye is added dropwise onto the surface of the eye or into the conjunctival sac. After opening and closing the eye several times, preferably two to four times, to ensure thorough mixing, a filter paper, preferably fixed to a carrier strip, is laid on the inner surface of the lower eyelid with the carrier strip facing the lid.

During the tear removal, the eye can remain either open or closed, with the latter being preferred. After from 2 to 300 seconds, preferably 30 seconds, the filter strip is removed and can be used for determining components.

It is also possible to obtain the fluid from the filter by centrifugation, for example by laying it on an 0.2 $\mu m$ membrane ("Centricon$^R$" tubes) in order to remove cellular components and subsequently analyzing the fluid for example by chromatography, electrophoresis, ELISA or RIA. Use can also be made of the development or liberation of reagents or dyes on or in the filter and their quantification, for example by means of reflectance photometry. Since the lacrimal fluid can also reflect the constitution of the blood—these fluids communicate with each other by way of a filter system—for example the glucose level, the process described can also be used for quantifying soluble blood constituents.

The isolation of the lacrimal fluid can be followed by quantification of components, preferably determination of enzyme activities or concentrations, particularly preferably of protease activities or concentrations (e.g. urokinase, t-PA, plasmin, collagenases, cathepsins, thrombin or kallikrein).

The sampling kit according to the invention is suitable for obtaining lacrimal fluid both from humans and from other species, with subsequent qualitative and quantitative determination of measurement parameters.

The sampling kit and its use will be described taking the determination of the concentration and activity of the protease plasmin as an example:

EXAMPLE 1

Materials
Filter paper (sterilized by autoclaving)
MN 818 (®Macherey-Nagel; Düren/Germany 6×5 mm), fixed on a plastic strip (6×90 mm), with the filter paper protruding 1 mm beyond the edge of the plastic strip.
Dropping solution
Sterile isotonic NaCl solution
Buffer
40 mM HEPES, 280 mM NaCl, 8 mM KCl, 2 mM $MgCl_2$, 0.5 g/l polyoxyethylene glycol dodecyl ether, pH 7.5
Enzyme substrate
H-D-Val-Leu-Lys-pNAx2HCl
S-2251 (from Kabi)
Plasmin standard
Sub-Standard BW lot: 929891, calibrated on 2nd IRP 77/588 NIBSC
Collection of the lacrimal fluid 20 μl of sterile isotonic NaCl solution are added dropwise to the surface of the eye or into the (drawn-back) conjunctival sac (lower lid); the lids are blinked 3 times (thorough mixing);

The test strip is laid on the lower lid, with the plastic material being located underneath (lying on the lid). The surface of the eye (cornea/conjunctiva) should not be touched;

The eye is closed for 30 sec.;

The filter strip, which has absorbed as much as it can, is removed and the fluid adhering to the plastic is wiped off with a piece of absorbent paper;

The filter strip is placed in a prepared cuvette so that the strip does not lie in the "light path" of the cuvette. The filter paper faces the lumen of the cuvette. The cuvette is incubated at 37° C.

Determination of the plasmin activity

The plasmin activity is determined photometrically at 405 nm by cleavage of the chromogenic substrate S-2251 and liberation of para-nitroanilide. The plasmin activity is quantified with the aid of a calibration curve constructed using standard plasmin.

The standard curve is constructed by applying filter strips for approximately 10 sec. to the standard solution which has been prepared (approximately 1 mm dipped in), wiping off the excess fluid from the plastic, and introducing the strip into the cuvette.

The cuvettes are prepared by pipetting in each case 150 μl of distilled water and 240 μl of HEPES buffer.

Following the addition of 100 μl of substrate solution (4 mM), the OD 405 nm is measured after different incubation times. In order to facilitate positioning in the photometer, that plastic part of the carrier protruding above the edge of the cuvette can be removed.

In order to cover as wide a measurement range as possible, the standard curve, which is prepared once, and the samples can be measured at several time points. In this example, the plasmin activity can be determined in a measurement range of from 0.05 to 100 μg/ml. When using the given conditions, measured after 15, 60 and 240 min. (see FIG. 1).

The plasmin activity and concentration are quantified using the standard curve (in a linear measurement range which can readily be evaluated). It is advisable to use different measurement ranges after different incubation times:

| 15 min. incubation | 2.0 IU/ml | −0.2 IU/ml |
|---|---|---|
|  | 100.0 μg/ml | −10.0 μg/ml |
| 60 min. incubation | 0.2 IU/ml | −0.02 IU/ml |
|  | 10.0 μg/ml | −1.0 μg/ml |
| 240 min. incubation | 0.02 IU/ml | −0.002 IU/ml |
|  | 1.0 μg/ml | −0.1 μg/ml |

Incubating for >12 hours makes it possible to quantify plasmin levels which are even <0.002 IU/ml (<0.1 μg/ml).

Result

Standard curves (FIG. 1)

Figure 2:
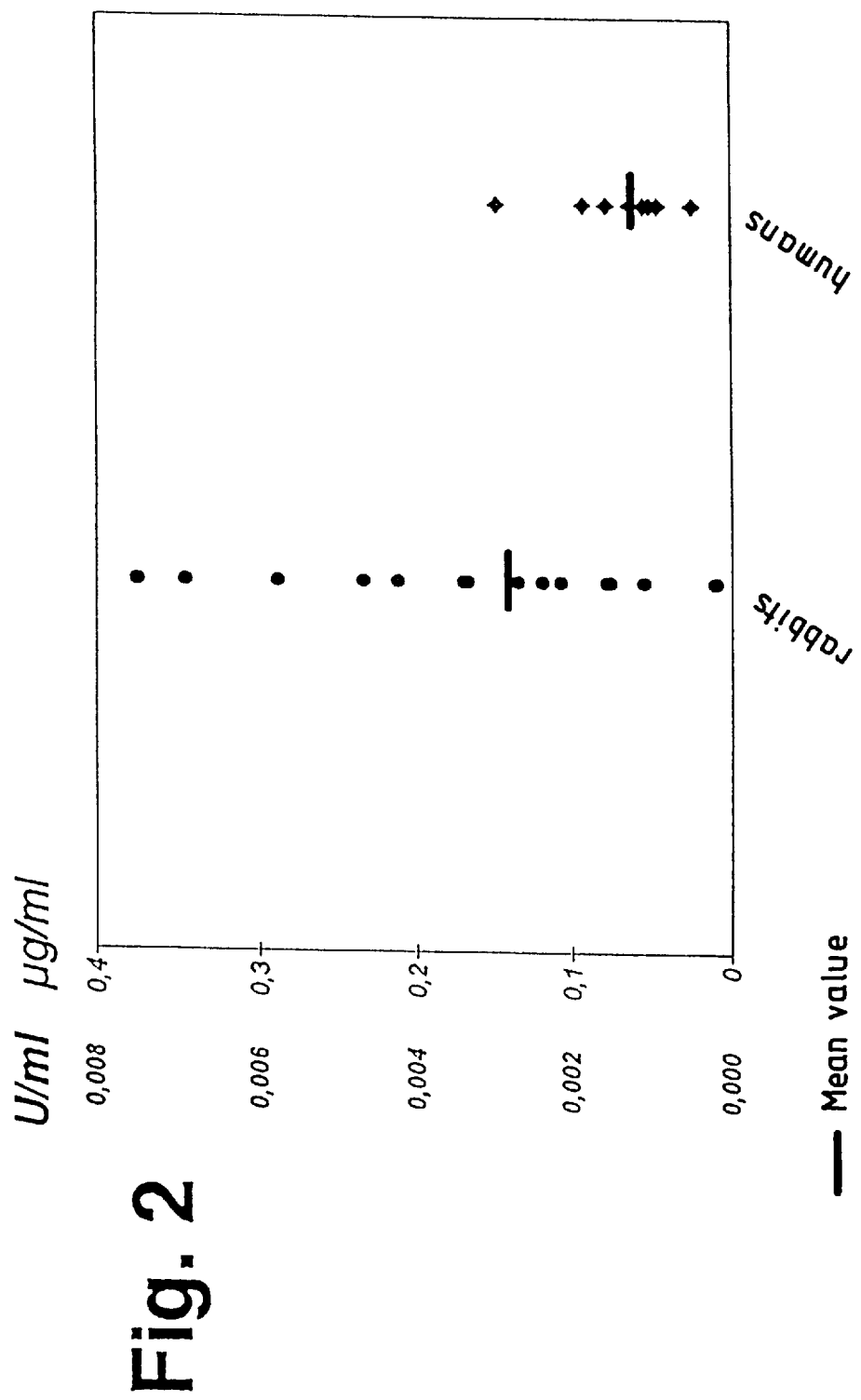
FIG. 2 shows the detection of plasmin in lacrimal fluids obtained from rabbits and from humans.

"Normal values" for humans and rabbits were determined, as depicted in FIG. 2.

Despite the scatter of the individual values, these normal values can be used for distinguishing pathological conditions since the pathological values are several times greater.

A similar approach can be used, for example, with other proteases and other enzymes as well.

We claim:

1. A method for reproducibly determining components of lacrimal fluid, comprising the steps of:

(a) applying a first defined volume of a fluid, which is well-tolerated by an eye, to the surface of the eye or into a conjunctival sac of the eye to amplify the lacrimal fluid, wherein the first defined volume is matched to a tear volume required for use for determining components of the lacrimal fluid and wherein the first defined volume remains in contact with the surface of the eye and conjunctival sac;

(b) removing a second defined volume of the amplified lacrimal fluid using an absorbent material that has size dimensions such that a maximum absorbable volume is exceeded by the quantity of amplified lacrimal fluid, wherein said absorbent material does not touch the surface of the eye; and (c) determining components of the amplified lacrimal fluid.

2. The process as claimed in claim 1, wherein the first defined volume is between 1 and 500 μl.

3. The process as claimed in claim 2, wherein the first defined volume of fluid is between 2 to 200 μl.

4. The process as claimed in claim 2, wherein the first defined volume of fluid is between 3 to 100 μl.

5. The process as claimed in claim 2, wherein the first defined volume of fluid is between 5 to 30 μl.

6. The process of claim 1, wherein the determination of the components of the amplified lacrimal fluid is performed by chromatography, electrophoresis, ELISA, RIA, reflectance photometry, or an assay that determines enzyme activity or enzyme concentration.

7. The process as claimed in claim 1, wherein the eye belongs to a human.

8. The process as claimed in claim 1, wherein the absorbent material is a filter strip.

9. The process as claimed in claim 8, wherein the filter strip is attached to a carrier strip.

10. The process as claimed in claim 9, wherein the second defined volume is removed by laying the filter strip attached to the carrier strip on an inner surface of a lower eyelid with the carrier strip facing the lower eyelid.

11. The process as claimed in claim 1, wherein the eye remains closed during removal of the second defined volume.

12. The process as claimed in claim 1, wherein the absorbent material remains in contact with the eye for 2 to 300 seconds.

13. The process as claimed in claim 12, wherein the absorbent material remains in contact with the eye for about 30 seconds.

14. The process as claimed in claim 1, wherein the first defined volume is added dropwise and the eye is subsequently opened and closed several times.

15. The process as claimed in claim 14, wherein the eye is opened and closed two to four times.

* * * * *